US00PP11617P

United States Patent [19]

Zary

[11] Patent Number: Plant 11,617

[45] Date of Patent: Nov. 7, 2000

[54] HYBRID TEA ROSE PLANT NAMED 'JACFEHON'

[75] Inventor: Keith W. Zary, Thousand Oaks, Calif.

[73] Assignee: Bear Creek Gardens, Inc., Medford, Oreg.

[21] Appl. No.: 09/234,786

[22] Filed: Jan. 20, 1999

[51] Int. Cl.[7] ..... A01H 5/00

[52] U.S. Cl. ..... Plt./134

[58] Field of Search ..... Plt./130, 134, 135

*Primary Examiner*—Howard J. Locker

*Attorney, Agent, or Firm*—Klarquist Sparkman Campbell Leigh & Whinston, LLP

[57] ABSTRACT

Hybrid rose plant having novel apricot colored flowers of large size on long stems; a long vase life; and large foliage.

1 Drawing Sheet

The present invention relates to a new and distinct variety of rose plant of the hybrid tea rose class which was originated by me by crossing the variety 'JACyem', U.S. Plant Pat. No. 9,329, with an unnamed seedling ('JAColite' (U.S. Plant Pat. No. 4,167)×'KORlingo' (U.S. Plant Pat. No. 5846).

The primary objective of this breeding was to produce a new rose variety having the long stems, large flowers, and fragrance of the female parent combined with the good vase life and large foliage of the male parent. It was hoped flower color would segregate in the yellows or yellow blends.

The objctive was substantially achieved, along with other desirable improvements, as evidenced by the following unique combination of characteristics that are outstanding in the new variety and that distinguish it from its parents, as well as from all other varieties of which I am aware:

1. Novel apricot flower color;
2. Long stems;
3. Large flower size;
4. Fragrance;
5. Good vase life, and;
6. Large foliage.

'JACfehon' is a long-stemmed, greenhouse cut rose. Stems average 24–28" long with production 170–180 stems/$m^2$ of greenhouse. Vase life is twelve to fourteen days.

Asexual reproduction of this new variety by budding, as performed at Wasco, Calif., shows that the foregoing and all other characteristics and distinctions come true to form and are established and transmitted through succeeding propagatons.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.13* 'JACyem' (U.S. Plant Pat. No. 2329).

*Pollen parent.*—Unnamed seedling, ('JAColite'× 'KORlingo').

Classification:

*Botanical.* —*Rosa hybrida*.

*Commercial.*—Hybrid Tea.

FLOWER

Observations made from specimens grown in a greenhouse environment at Somis, Calif., February 1997 to December 1998.

Blooming habit: Continuous.

Bud:

*Size.*—Two and one-quarter inches long when the petals start to unfurl.

*Form.*—The bud form is long, pointed ovoid.

*Color.*—When sepals first divide, bud color is Yellow-Green Group 154C at the base of the bud and extending upward. The tip of the bud is close to Yellow-Orange Group 22C and extending downward. When half blown, the upper sides of the outer petals are close to Yellow-Orange Group 19C on the outer two-thirds of a petal and Yellow Group 12B on the inner one-third. On the inner petals, the outer one-quarter of a petal is Orange Group 24D; the inner three-quarters is Yellow Group 12B. Lower sides of the outer petals are Yellow-Orange Group 19C on the outer two-thirds of a petal and Yellow Group 12B on the inner one-third of a petal. On the inner petals, the lower surface of a petal is Orange Group 24D on the outer one-quarter and Yellow Group 12B on the inner three-quarters.

*Sepals.*—Color: Green Group 138B. Surface texture: Covered in fine hairs. There are three heavily appendaged sepals. There are two unappendaged sepals with hairy edges.

*Receptacle.*—Color: Green Group 137C. Shape: Funnel. Size: Medium, about ½"×7/16". Surface: Smooth.

*Peduncle.*—Length: Long, averaging about five inches. Surface: Glandular. Color: Green Group 137B. Strength: Stiff, erect, heavy.

Bloom:

*Size.*—Large. Average open size is five inches.

*Borne.*—Singly.

*Stems.*—Strength: Strong. Average length is about twenty-four to twenty-eight inches.

*Form.*—When first open: High-centered. Permanence: Retains its form to the end. Outer petals curl back, quill fashion.

*Petalage.*—Number of petals under normal conditions: 30–35.

*Color.*—The upper sides of the petals: Outer petals are close to Yellow-Orange Group 19C on the outer two-thirds of a petal and Yellow Group 12B on the inner one-third of a petal. Inner petals are Orange Group 24D on the outer one-quarter of a petal and Yellow Group 12B on the inner three-quarters of a petal. The reverse sides of the petals: Outer petals are Yellow-Orange Group 19C on the outer two-thirds of a petal and Yellow Group 12B on the inner one-third of a petal. Inner petals are Orange Group 24D on the outer one-quarter of a petal and Yellow Group 12B on the inner three-quarters of a petal. The base of each petal has, on the upper surface, a ¼"×¼", Yellow Group 13A color spot. The lower surface has a 3/16"×3/16" Yellow Group 13A color spot. The major color on the upper side is Yellow Orange Group 19C on the outer part; Yellow Group 12B on the inner part.

*Variegations.*—There is a Green Group 143C streak on the guard petal midrib that is most prevalent on the upper petal surface.

*Discoloration.*—The general tonality at the end of the first day: No change. At the end of the third day: No change. By day five, in the vase, there is a general fading to Yellow-Orange Group 19C on both petal surfaces. This fading increases slowly through day twelve in the vase until all petals are Yellow-Orange Group 19C on the outer two-thirds of the petal and Yellow Group 12B on the inner one-third on the upper surface. The lower surface also fades slowly until all petals are Orange Group 24C on the outer two-thirds and Yellow Group 12B on the inner one-third.

*Fragrance.*—Moderate, spicy.

Petals:

*Texture.*—Thick.

*Shape.*—Round.

*Form.*—Tips slightly recurved, edges slightly quilled.

*Arrangement.*—Imbricated. Petaloids in the center: None.

*Persistence.*—Petals drop off cleanly before drying.

*Lastingness.*—On the plant: Long (seven to eight days). As a cut flower: Long (about twelve to fourteen days).

Reproductive parts:

*Anthers.*—Size: Medium. Quantity: Many. Color: Orange-Yellow Group 17B. Arrangament: Regular around styles.

*Filaments.*—Orange-Yellow Group 17B.

*Pollen.*—Present.

*Styles.*—Color: Greyed-Purple Group 183D

*Stigmas.*—Color: Yellow-White Group 158C. .

Plant:

*Form.*—Shrub.

*Growth.*—Very Vigorous. Mature plant height is about seven feet, width is about 4½ feet.

Foliage: Number of leaflets on normal mid-stem leaves: Five or seven.

*Size.*—Very Large (8" long×6" wide).

*Quantity.*—Abundant.

*Color.13* New foliage: Upper and lower surfaces: Greyed-Red Group 178B. Old foliage: Upper surface: Green Group 137A. Lower surface: Green Group 138B.

Leaflets:

*Shape.*—Pointed oval.

*Texture.*—Leathery.

*Edge.*—Serrated.

*Serration.*—Single, small.

*Petiole rachis.*—Green Group 139C.

*Petiole underside.*—Smooth.

*Stipules.*—Long (¾"), serrated, bearded.

*Disease resistance.*—Resistant to mildew and rust under normal growing conditions in a greenhouse. Not tested for blackspot.

Wood:

*New wood.*—Color: Green Group 145C. Bark: Smooth

*Old wood.*—Color: Green Group 137B. Bark: Smooth.

Prickles:

*Quantity.*—On main canes from base: Ordinary. On laterals from main canes: Ordinary.

*Form.*—Medium, hooked downward.

*Color when young.*—Greyed-Red Group 178A.

*Color when mature.*—Greyed-Orange Group 166A.

Small prickels:

*Quantity.*—On main stalks: None. On laterals: None.

I claim:

1. A new and distinct variety of rose plant of the hybrid tea class, substantially as herein shown and described, characterized particularly by the novel apricot color of its large flowers having good vase life, its long stems and its large foliage.

* * * * *

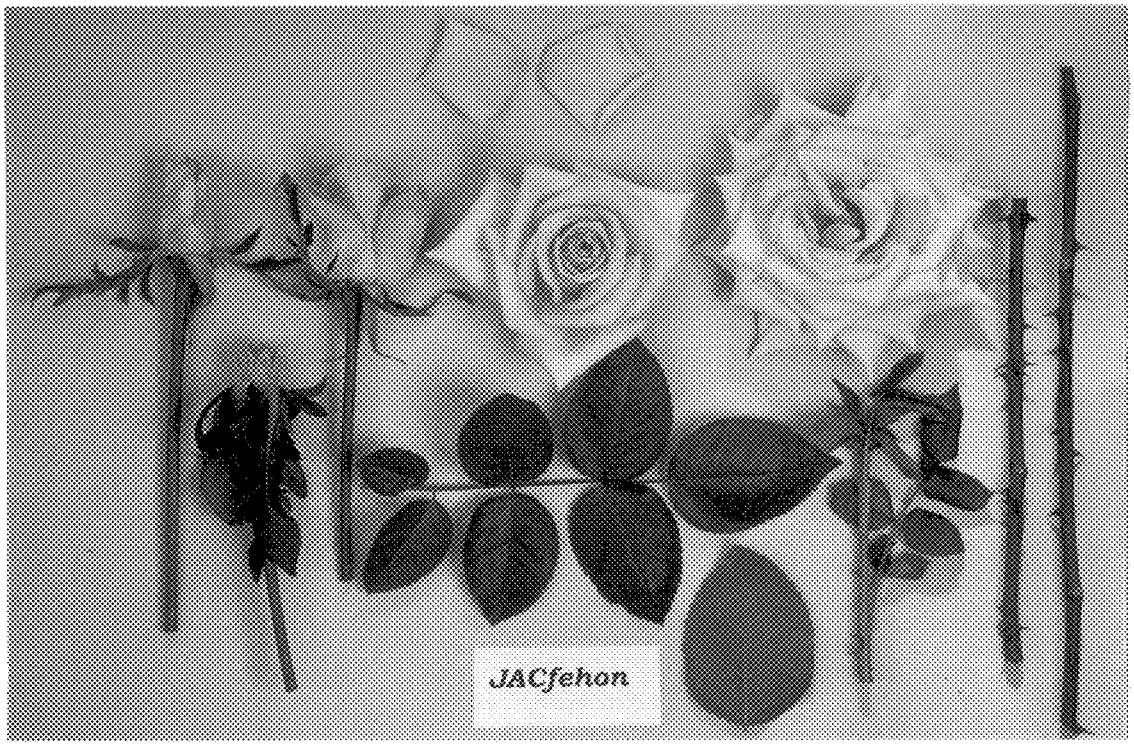
JACfehon

UNITED STATES PATENT AND TRADEMARK OFFICE

CERTIFICATE OF CORRECTION

PATENT NO. : PP 11,617
DATED : November 7, 2000
INVENTOR(S) : Keith W. Zary Ph.D.

It is certified that error appears in the above-identified patent and that said Letters Patent is hereby corrected as shown below:

Column 1,
Line 41, change "seed parent ... Pat. No. 2329" to -- seed parent ... Pat. No. 9329 --, as shown in page 1, line 7 of the Application.

Column 4,
Line 24, change "145C" to -- 146C --, as shown in page 8, line 3 of the Application.

Signed and Sealed this

Eleventh Day of December, 2001

*Attest:*

Nicholas P. Godici

NICHOLAS P. GODICI
*Acting Director of the United States Patent and Trademark Office*

*Attesting Officer*